United States Patent
Narusawa et al.

(10) Patent No.: US 6,168,431 B1
(45) Date of Patent: Jan. 2, 2001

(54) METHOD OF POLYMERIZING PHOTO-POLYMERIZABLE COMPOSITION FOR DENTAL USE AND DENTAL LIGHT-CURING APPARATUS FOR USE THEREWITH

(75) Inventors: Hideaki Narusawa, Tokyo; Kenichi Hino, Kurashiki; Fumihiko Ohtani; Masahiro Ihara, both of Kyoto, all of (JP)

(73) Assignees: Kuraray Co., Ltd., Kurashiki; Shimadzu Corporation, Kyoto, both of (JP)

(*) Notice: Under 35 U.S.C. 154(b), the term of this patent shall be extended for 0 days.

(21) Appl. No.: 09/401,411

(22) Filed: Sep. 22, 1999

Related U.S. Application Data

(63) Continuation of application No. 08/932,463, filed on Sep. 18, 1997, now Pat. No. 6,033,223.

(30) Foreign Application Priority Data

Sep. 20, 1996 (JP) .................................................. 8-271389

(51) Int. Cl.[7] ................................ A61C 1/00; A61C 3/00
(52) U.S. Cl. ............................................ 433/29; 433/226
(58) Field of Search ........................... 433/29, 141, 215, 433/226, 228.1, 229

(56) References Cited

U.S. PATENT DOCUMENTS

| | | | |
|---|---|---|---|
| 4,666,406 | * 5/1987 | Kanca, III | 433/228.1 X |
| 4,726,770 | * 2/1988 | Kurer | 433/215 X |
| 5,007,837 | * 4/1991 | Werly | 433/29 X |
| 5,312,249 | * 5/1994 | Kennedy | 433/29 |
| 5,759,032 | * 5/1987 | Bartel | 433/29 |
| 5,797,740 | * 8/1998 | Lundvik | 433/29 |

* cited by examiner

*Primary Examiner*—Nicholas D. Lucchesi
(74) *Attorney, Agent, or Firm*—Oblon, Spivak, McClelland, Maier & Neustadt, P.C.

(57) ABSTRACT

A method of polymerizing a photo-polymerizable dental composition with the use of a light-curing apparatus including a light source (1) for emitting a laser beam and an optical fiber (2) optically coupled with the light source (1) and having a light emitting element (5) opposite to the light source (1). The photo-polymerizable dental composition (M) is filled in a dental cavity (H), and the light emitting element (5) of the optical fiber (2) is subsequently introduced in the filled photo-polymerizable dental composition (M) to a position adjacent a bottom of the dental cavity (H). Thereafter, the filled photo-polymerizable dental composition (M) is irradiated with the laser beam of 350 to 500 mm in wavelength at 10 to 100 mW, to cause the filled photo-polymerizable dental composite (M) to initiate polymerization progressively from a portion thereof adjacent the bottom of the dental cavity (H) towards a surface portion thereof.

7 Claims, 4 Drawing Sheets

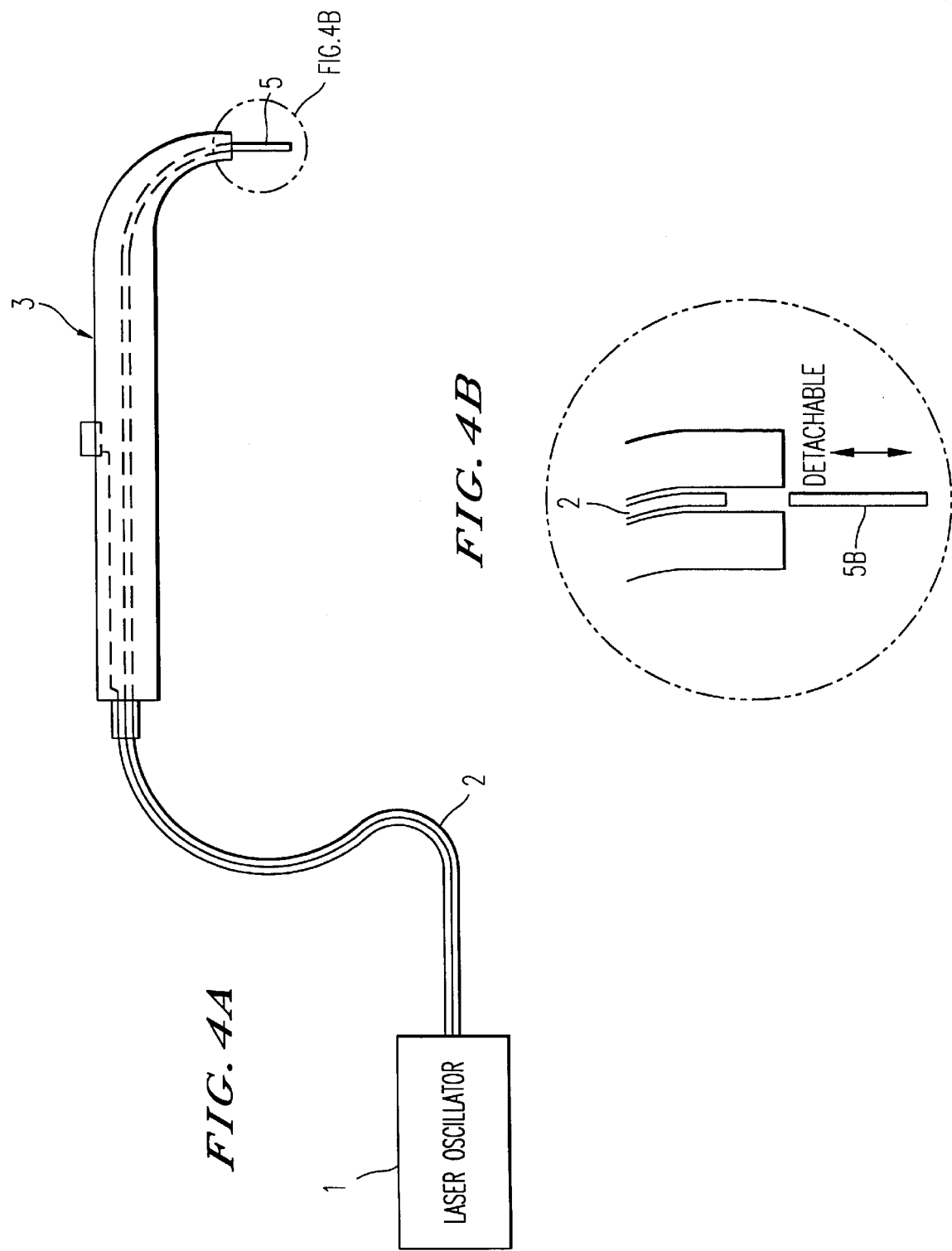

METHOD OF POLYMERIZING PHOTO-POLYMERIZABLE COMPOSITION FOR DENTAL USE AND DENTAL LIGHT-CURING APPARATUS FOR USE THEREWITH

This application is a Continuation of 08/932,463 filed Sep. 18, 1997 now U.S. Pat. No. 60/332,23.

BACKGROUND OF THE INVENTION

1. Field of the Invention

The present invention relates to a method of polymerizing a photo-polymerizable composition for dental use, which may be used in filing treatment of dental caries, and also to a beam illuminator for use in filling treatment of the dental caries with the photo-polymerizable composition.

2. Description of the Prior Art

In recent years, the polymerizable dental compositions (composite resins) comprising a polymerizable monomer, a polymerization initiator and an inorganic filler have been improved in physical strength resistance to wear color rendering and reproducibility of a tooth morphology and has therefore been used widely not only in dental filling treatment of dental caries and as a material for dental crowns, but also in many other applications. Among others the photo-polymerizable composite resin which initiates polymerization with visible light irradiation has expanded its market because of its ease to use and handle and is now one of the most popular products.

However, the polymerizable composite resin has been found having its own problem, that is, polymerization shrinkage. Specifically, when the photo-polymerizable composite resin undergoes polymerization, a considerably large shrinkage stress develops, resulting in formation of a gap between the eventually polymerized composite resin and the cavity wall. The shrinkage stress is related to a pain that a patient may feel during the dental treatment, and the gap between the polymerized composite resin and the cavity wall often constitutes a cause for loss of the dental filling and generation of secondary caries. Accordingly, attempts have been made to avoid formation of the gap, but have not yet been successful.

With regard to the light-curing apparatus, the currently utilized popular light-curing apparatus comprises a light source installing a halogen-tungsten lamp, a control means including a switch for controlling the light source and a timer for setting the duration of irradiation, a cooling means with a cooling fan, and a light guide means including optical fibers bundled to a diameter of 6 to 16 mm, and is so designed as to irradiate downwardly the photo-polymerizable composite resin filled in the dental cavity with a broad light of a high intensity. Polymerization of the photo-polymerizable composite resin with the above-mentioned light-curing apparatus has been found making it difficult to eliminate the problem of the gap and cracking resulting from the polymerization shrinkage of the photo-polymerizable composite resin.

By way of example, when the photo-polymerizable composite resin filled in a cylindrical dental cavity is irradiated from above by the visible rays of light emitted from the light-curing apparatus, an upper portion of the photo-polymerizable composite resin will be cured upon polymerization to close the cavity photo-polymerizable composite resin proceeds deep into the dental cavity. The formation of the gap and cracking is, however, found unavoidable because of the polymerization shrinkage. The higher intensity of the light to irradiate, the quicker the photo-polymerization. Accordingly, the quicker the photo-polymerization, the faster the shrinkage of the photo-polymerizable composite resin and, hence, the easier the formation of the gap and cracking.

Also, with the method in which the photo-polymerizable composite resin filled in the dental cavity is irradiated from above the dental cavity, it is impossible for a dentist to ascertain whether or not the photo-polymerizable composite resin in the dental cavity would have been completely polymerized to cure, and it has often occurred that the bottom portion of the photo-polymerizable composite resin in the dental cavity remains unpolymerized. Once this occurs, there is a risk that a monomer component of the unpolymerized composite resin will penetrate in a high concentration into the dental pulp.

In view of the foregoing problems, the Japanese Laid-open Patent Publication No. 64-15037, published in 1989, discloses a shrinkage-compensated differential photo-polymerizing method. According to this publication, two kinds of photo-polymerizable composite resins sensitive to different wavelengths of light were prepared. The first photo-polymerizable composite resin is applied to the wall of the dental cavity, followed by filling of the second photo-polymerizable composite resin. Thereafter, the second photo-polymerizable composite resin is first polymerized by irradiation, followed by photo-polymerization of the first photo-polymerizable composite resin. The method disclosed in the publication is described effective to minimize any possible adverse effect brought about on the teeth by the shrinkage occurring upon polymerization within the cavity.

It appears that the method disclosed in the publication referred to above has the following two features: In the first place if the second photo-polymerizable composite resin, which is the major filling material, is first polymerized prior to curing of the first photo-polymerizable composite resin which corresponds to a material for protecting the cavity wall and which is used in a relatively small quantity, the polymerization shrinkage occurring in the second photo-polymerizable composite resin can be compensated for by flow or deformation of the first photo-polymerizable composite resin so that shrinkage of the second photo-polymerized composite resin can complete without adversely affecting the teeth.

In the second place, even though the first photo-polymerizable composite resin used in the relatively small quantity, is polymerized subsequently, an averse influence on the teeth which would be brought about by shrinkage of the first photo-polymerizable composite resin would be minimal so long as it is used in a small quantity.

However, not only has the publication referred to above failed to specify particular materials and compositions used for this purpose, but also the processes disclosed therein are indeed complicated, and therefore, the technical effectiveness of the method disclosed therein is questioned. Specifically, considering that the polymerizable dental composite resin is in the form of a slurry or a paste, and even though the cavity wall is protected by the first photo-polymerizable composite resin, an attempt to fill up such a small hole as the caries cavity with the second photo-polymerizable composite resin is quite difficult to accomplish without allowing the first photo-polymerizable composite resin to flow or deform, and the portal edge of the cavity would be more or less covered by the second photo-polymerizable composite resin. In other words, when the second photo-polymerizable composite resin is cured first by polymerization, such composite resin will form a cover over the opening of the dental cavity, making it difficult to avoid developing polymerization shrinkage stresses inside the dental cavity.

In addition, the first and second photo-polymerizable composite resins are described as initiating polymerization upon irradiation with the respective light of different wavelengths. However, the photo-polymerization initiator is generally not sensitive selectively to a certain single wavelength, but sensitive to a relatively broad band of wavelengths. Further in the light-curing apparatus utilizing a halogen lamp, the light emitted therefrom have a broad band of wavelengths. Accordingly, it is difficult to assuredly prevent the first photo-polymerizable composite resin from initiating its polymerization when the second photo-polymerizable composite resin is photo-polymerized and therefore, it is not avoidable that the second photo-polymerizable composite resin eventually forms a cover over the dental cavity opening.

By the reasons as discussed above, the suggestion disclosed in the publication referred to above appears having numerous problems left unsolved.

On the other hand, the inventors of the present invention have conducted a series of experiments in which with the use of a light dispersive rod (LUCIWEDGE. available from Howe Neos Dental Inc.) a laser beam is introduced into the light dispersive rod through its light source end while a free end of the light dispersive rod opposite to the light source end is inserted into a lump of the composite resin. As a result, the inventors have found that while a substantial amount of the laser beam so introduced had been irradiated outwardly from the whole peripheral surface of the rod, the intensity of the laser beam irradiated was found higher at a location close to the light source end than at any other location remote from the light source end. As regards the extent to which the composite resin is polymerized by the laser beam, the inventors have also confirmed that a head portion of the composite resin was sufficiently cured, but a portion of the composite resin adjacent the free end of the rod was little cured.

Even in the experiments conducted by the inventors in which in place of the light dispersive rod a rod or tube made of transparent plastics was inserted in a lump of the composite resin, a result similar to that described above, that is, in which a portion of the composite resin adjacent the light source end of the rod was much polymerized, but a portion of the composite resin adjacent the free end of the rod was little cured, is obtained. This appears to have resulted from the fact that in the previously described light guide means, a substantial amount of the laser beam was scattered from a portion of the rod adjacent the light source end and the amount of the laser beam scattered from the free end of the rod was small.

Accordingly, with the conventional technique of introducing the laser beam into the composite resin, there is a tendency that only a portion of the composite resin adjacent the opening of the cavity and, hence, adjacent the light source is first cured and the remaining portion of the composite resin adjacent the bottom of the cavity does not cure sufficiently, and accordingly, the problem associated with development of the shrinkage stresses in the cavity wall during the polymerization has not yet been solved.

SUMMARY OF THE INVENTION

The present invention is therefore intended to provide a method wherein polymerization of the composite resin filled in the cavity in a tooth or a dental mold is initiated from a bottom portion of the filled composite resin to thereby substantially eliminate the problem associated with development of the polymerization shrinkage stresses of the composite resin in the cavity, and a light-curing apparatus for execution of such method.

Another important object of the present invention is to provide a method and a light-curing apparatus wherein a distal end of the dental light-curing apparatus is so disposable as to prevent a dentist from being infected by body fluids such as blood and saliva of the patient and also to prevent a patient from being infected by body fluids in re-use of the apparatus.

As an extensive study done by the inventors of the present invention to substantially eliminate the various problems hitherto encountered, it has been found that when a laser beam enters a photo-polymerizable dental composition (composite resin), the light tends to be considerably scattered by a filler included in the photo-polymerizable composite resin and spreads in a spherical form within the photo-polymerizable composite resin, that is, propagates not only in a direction of incidence, but also in a direction counter to the direction of incidence. It has also been found that the dentin has a characteristic of scattering the incident light as much as the photo-polymerizable composite resin and a substantial amount of the light incident on the bottom of the cavity is reflected towards the photo-polymerizable composite resin. The present invention is based on these findings.

The present invention provides a method of polymerizing a photo-polymerizable dental composition with a light-curing apparatus including a light source for emitting a laser beam and an elongated light guide means optically coupled with the light source and having a light emitting element opposite to the light source. At least the light emitting element is prepared from an optical fiber. According to this method, the photo-polymerizable dental composition is filled in a dental mold or a cavity, and the light emitting element of the optical fiber is subsequently introduced in the photo-polymerizable dental composition to a position adjacent a bottom of the cavity. Thereafter, the photo-polymerizable dental composition is irradiated with the laser beam of 350 to 500 mm in wave-length at 10 to 100 mW emitting from an end portion of the light emitting element, to cause the photo-polymerizable dental composite to initiate polymerization progressively from the bottom portion of the cavity towards a surface portion thereof.

The light emitting element prepared from the optical fiber may be cut at a position adjacent a surface of the cured photo-polymerizable dental composition to leave the distal end of the optical fiber in the cured photo-polymerizable dental composition within the cavity. Alternatively, where the optical fiber having a surface having no affinity to the photo-polymerizable dental composition is used, the optical fiber may be removed from the cured photo-polymerizable dental composition after the latter has been polymerized to cure, and a hollow, left in the cured photo-polymerizable dental composition by removal of the optical fiber may subsequently be filled up with the photo-polymerizable dental composition which is then irradiated from above to cure.

The present invention also provides a dental light-curing apparatus which comprises a light source for generating a laser beam of 350 to 500 mm in wavelength at 10 to 100 mW (milliwatt), and an elongated light guide means having a proximal end optically coupled with the light source and also having a light emitting element at a distal end thereof.

At least said light emitting element is an optical fiber and adapted to be introduced into a photo-polymerizable dental composition filled in a cavity in a dental mold or a tooth to irradiate the photo-polymerizable dental composition at a location adjacent a bottom of the cavity.

The light emitting element may be an integral part of the light guide means, that is, the distal end of the light guide means or may be a member separate therefrom. In case the light emitting element is a member separate from the light guide means, the dental light-curing apparatus may further comprise a detachable optical coupling mechanism interposed between the light emitting element and the distal end of the light guide means to permit the light emitting element to be selectively coupled to and decoupled from the light guide means In case the light emitting element is the distal end of the optical fiber forming the light guide means, the light-curing apparatus may further comprise a cutting mechanism provided in the vicinity of the distal end for cutting to separate the distal end from a remaining portion of the optical fiber.

Said light emitting element has a surface which may have an affinity or no affinity to the photo-polymerizable dental composition.

The light-curing apparatus may further comprise a contamination-preventive covering to prevent the light guide means from being contaminated by body fluids.

In the practice of the method of the present invention, a dentist after having formed a cavity in a tooth left by removal of a caries-infected region of the tooth has to apply a bonding agent, available as an accessory to the photo-polymerizable dental composite resin, followed by filling in the cavity of the photo-polymerizable dental composite resin, a volume of which is slightly smaller than that of the cavity. Thereafter, the light guide means of the light-curing apparatus of the present invention is introduced into the patient's mouth with the light emitting element at the distal end of the light guide means introduced deep into the filled composite resin within the cavity. At this time, the optical fiber forming the light emitting element is inserted to a position which may contact the bottom of the cavity or may be adjacent the bottom of the cavity. The filled composite resin is then irradiated by the light emerging from an end portion of the optical fiber for a predetermined length of time required to accomplish polymerization of the composite resin.

After the polymerization, the optical fiber is removed from the cavity or is allowed to remain within the cavity by cutting the optical fiber to separate the distal end of the optical fiber. The light guide means is then removed out of the patient's mouth.

The light-curing apparatus according to the present invention comprises the light source, a control means for the light source, the light guide means and the light emitting element which may either an integral part of or a member separate from the light guide means.

Where the optical fiber is left as inserted into the cavity, the optical fiber is cut at a location adjacent a surface of the composite resin filled within the cavity is severed. Thereafter, an additional amount of the photo-polymerizable composite resin required to restore the affected tooth to a shape similar to the original shape is deposited over the cured composite resin to form a resin overlay which is subsequently irradiated from above with the light to cause the additional photo-polymerizable composite resin to polymerize. After a complete curing, the cured composite resin is finely adjusted and ground to complete the dental restoration.

It is to be noted that preparation of a dental prosthesis with the use of the dental mold can be accomplished in a manner similar to that described above. In such case, the photo-polymerizable composition is filled in the cavity of the mold, which is subsequently polymerized to cure with the light-curing apparatus of the present invention.

The method of the present invention when practiced with the dental light-curing apparatus of the present invention brings about the following advantages.

1. Since the photo-polymerizable composite resin filled in the cavity in the tooth or the dental mold polymerizes progressively from the bottom of the cavity towards the surface of the cavity, there is no possibility that a portion of the photo-polymerizable composite resin will not be left uncured at the bottom of the cavity, and the photo-polymerizable composite resin in its entirety can be completely cured.

2. The risk of the bonding layer being destroyed at the bonding interface between the photo-polymerizable composite resin and the tooth, which would occur with the polymerization shrinkage stresses can be advantageously minimized to accomplish a firm bonding between the composite resin and the tooth with minimal loss of the cured composite resin from the cavity.

3. No formation of a gap occurs between the photo-polymerizable composite resin and the tooth and, therefore, no site of proliferation of caries-causative bacteria is formed to thereby avoid the possibility of recurrence of the dental caries.

4. Even if the affected site is located deep in the tooth, there is no possibility that a portion of the photo-polymerizable composite resin adjacent the bottom of the cavity will be left unpolymerized, and therefore, the risk of some components of the photo-polymerizable composite resin penetrating into the dental pulp can be almost completely reduced.

5. Since irradiation takes place from the optical fiber introduced into the cavity, there is no possibility that the light is radiated outwardly from the mouth and there is not hazardous condition in which the dentist's eyes may be affected by irradiation of a high intensity of light.

6. Since the light emitting element is disposable and the handpiece is sterilizable for reuse for each patient, cross-infection of the dental diseases between patients can be avoided. A disposable covering for the light emitting element is more preferable to the same purpose.

The optical fiber employed in the practice of the present invention may be prepared from either acrylic plastics or quartz. However, the acrylic resin is preferred as a material for the optical fiber since it can be available at a low cost and it can exhibit a favorable affinity with the photo-polymerizable composite resin because the latter is prepared from an acrylic compound.

Where a portion of the optical fiber is allowed to be left in the cured composite resin, the optical fiber is preferably having an affinity surface to the photo-polymerizable composite resin used to enhance a bonding between the eventually cured composite resin and the optical fiber. Unless a satisfactory bonding is achieved between the optical fiber and the cured composite resin, microgaps would be formed at the bonding interface and a secondary caries infection would be likely to occur.

Where the optical fiber is prepared from the acrylic plastics, the surface having an affinity may be the optical fiber per se. However, where quarts is used as a material for the optical fiber, the surface of the optical fiber can have an affinity to the photo-polymerizable composite resin with a silane coupling agent to form a coating.

Where the optical fiber is removed from the cured composite resin, the optical fiber is preferably having a surface having no affinity to the photo-polymerizable composite resin to facilitate a smooth removal of the optical fiber from the cured composite resin. The surface having no affinity can be formed by coating the surface of the optical fiber with any of polyolefines of non-polarity, synthetic rubbers or fluorine-containing polymers.

In the event that a hollow is formed as a result of removal of the optical fiber, the hollow need be sufficiently filled up with the photo-polymerizable composite resin.

The light source used in the light-curing apparatus of the present invention may be a laser of a type capable of emitting a laser beam of 350 to 500 nm in wavelength. Preferably, the laser referred to above may be a solid state laser comprising a semiconductor using Nd:YAG (Nd:$Y_3Al_5O_{12}$) as a laser medium and capable of being oscillated emit a beam of 946 nm in wavelength, and a resonator using KN($KNbO_3$) which is a non-linear optical crystal to oscillate a secondary harmonic wave (473 nm). The solid state laser of the structure described above is referred to as a secondary harmonic light source of a resonator built-in type.

Alternatively, the light source may be a semiconductor laser capable of emitting a laser beam of 350 to 500 nm in wavelength or a lamp such as a halogen-tungsten lamp or a metal halide lamp. Where the lamp is employed, care must be taken to avoid application of heat to the affected site and, for this purpose, an infra-red cut-off filter may be employed to the lamp.

Also, in place of the laser, an array of light emitting diodes may be employed, in which case light emitted from the LED array must be converged.

Selection of the light of the wavelength within the range of 350 to 500 nm is based on the following reasons: If the wavelength of the light is shorter than 350 mn, the patient would be adversely affected by ultraviolet rays, but if the wavelength of the light is longer than 500 nm photo-polymerization would not be initiated. Also, as regards the intensity of the light, 10 to 100 mW is needed where the laser is employed for the light source, but 10 to 200 mW is needed where the lamp is used for the light source. Since the laser beam is a coherent beam and can exhibit an excellent characteristic in curing the photo-polymerizable composite resin, the intensity of the laser beam may be lower than that of the light from the lamp for accomplishing a photo-polymerization of the composite resin. In either case, if the intensity is lower than the lowermost limit, no photo-polymerization of the composite resin will be initiated, but if it is higher than the uppermost limit, the patient will adversely be affected by heat evolved by the light.

The control means used in the light-curing apparatus of the present invention may comprises a timer and/or a switch for controlling ON and OFF of the light source, selectively closing or opening an optical circuit from the light source to the light guide fiber, and setting a time during which irradiation is effected.

The light guide means employed in the light-curing apparatus of the present invention may be, for example, in the form of an optical fiber for conducting light from the light source to the optical fiber through a light collecting optical system so that the light can efficiently reach the light emitting element to be inserted into the cavity. The optical fiber forming the light guide means may be either a mono-filament or a multi-filament and may comprises a plurality of fiber segments optically coupled together.

In the practice of the present invention, it is important that the light emitting element to be inserted into the photo-polymerizable composite resin is formed by an optical fiber. When attempts have been made to insert a light dispersing rod, such as disclosed in the previously discussed Japanese publication No. 64-15037, or a transparent light guide rod having no light dispersing property, into the cavity filled with the photo-polymerizable composite resin, the light dispersing rod have scattered the incident light in all directions, failing to initiate the polymerization only from the bottom of the cavity and, on the other hand, the transparent rod have also failed to give a satisfactory result since a substantial amount of the incident light have leaked at the cavity opening.

In contrast thereto, the optical fiber does not emit the incident light from lateral surface thereof, but emit outwardly only from the end portion thereof opposite to the light source and, therefore, irradiation with the light can be satisfactorily effected progressively from the bottom of the cavity in the tooth or the dental mold. Also, since the optical fiber has an extremely small diameter, insertion, indwelling and removal of the optical fiber relative to the photo-polymerizable composite resin can easily be accomplished as compared with the use of the light dispersing rod.

The light emitting element in the form of an optical fiber which is inserted into the cavity is separable from the light guide means or easy to cut off so that a post-treatment to curing of the photo-polymerizable composite resin within the cavity can easily be performed. This light emitting element may be disposed of without being re-used.

One embodiment of the light-curing apparatus of the present invention comprises the light source and the light guide means in the form of a single continuous optical fiber, to which a fiber cutting mechanism is preferably added. This fiber cutting mechanism is to be positioned adjacent the distal end of the light guide means for cutting the distal end of the optical fiber from the remaining portion thereof so that the distal end of the optical fiber having been contaminated by the patient's blood and/or saliva as a result of the insertion into the dental cavity. Dental treatment with the use of a fresh optical fiber for each patient is most preferable.

Cutting of the optical fiber for the purpose discussed above may be carried out by the use of scissors or a knife. However, in terms of handling convenience, the cutting mechanism is preferably incorporated in a handpiece mounted on the optical fiber for the access by the dentist. By way of example, the handpiece may have a button which, by depressing, advances a blade to cut the optical fiber, or transmits a pushing force to a suitable rod to cut the optical fiber at a desired location by a blade provided at the tip portion of the rod.

A releasable coupling mechanism may be interposed between the light guide means and the light emitting element. However, the releasable coupling mechanism may likely to result in attenuation of the incident light travelling from the light guide means towards the light emitting element. Accordingly, the single continuous optical fiber is rather effective for maximized utilization of light.

The releasable coupling mechanism may have an adjuster and/or an adaptor effective to align the axis of optical fibers with each other.

The optical fiber used in the practice of the present invention must have such a diameter that when the optical fiber is inserted into the photo-polymerizable composite resin filled in the cavity, the composite resin will not be purged. Accordingly, the optical fiber is preferably of a diameter not greater than 1.5 mm, more preferably not greater than 1 mm, and most preferably not greater than 0.8 mm. The optical fiber used in the practice of the present invention may be either a mono-filament or a multi-filament, provided that it satisfies the diameter requirement discussed above. However, the use of the mono-filament for the optical fiber is preferred because of its low loss of light.

The length of the distal end of the optical fiber cannot be fixed because it is related to the design of the light guide means. However, where the light guide means has a handpiece by which the light guide means can be brought to a position close to the affected site, it is preferred that the optical fiber protrudes 5 mm or more out of a distal end of the handpiece. Where the distal end of the continuous optical fiber is inserted into the cavity at the affected site by holding the handpiece or by nipping the fiber by forceps or any other suitable nipping instrument, the optical fiber may have a total length of several meters. Where the optical fiber is of a substantial length, the use of a reel is preferred to wind up an excessive length of the optical fiber.

The shape of the optical fiber is related to the previously discussed length of the optical fiber. If the optical fiber protrudes about 5 mm distally from the distal end of the handpiece, the protruding portion may be straight. But where it has a substantial length exceeding about 5 mm and is handled by nipping it with the forceps, it may have a curvature of a diameter within the range of 10 to 50 mm.

the light-curing apparatus of the present invention is preferably of a design effective to avoid contamination by patient's blood and/or saliva. Since a distal portion of the light guide means is susceptible to such contamination it should be covered and, for this purpose, the handpiece may concurrently serve as a covering. Alternatively, a protective tubing may be provided on one side of the handpiece adjacent the light source for an additional covering, through which the light guide means is protected from being contaminated.

Again alternatively, an auxilary covering may be, singly or in combination with the above described covering, employed for covering the dentist's hand and the remaining portion of the light guide means except for the distal end thereof. With this covering, the light guide means and the dentist can be protected from being contaminated by patient's body fluids. This covering may be in the form of a bag made of a resinous sheet, within which the light guide means is passed while the dentist inserts his hand into the covering to grip the light guide means. The additional or auxiliary covering may be disposable after use for each patient.

The photo-polymerizable composite resin which can advantageously be employed in the practice of the present invention comprises a polymeriable monomer, a polymerization initiator, a filler material and suitable additives. The polymerizable monomer which can be employed in the photo-polymerizable composite resin includes monofunctional and/or polyfunctional (meth)acrylic acid esters including (meth)acrylic acid alkyl ester (the number of carbon atoms of the alkyl group being 1 to 10), polyalkyleneglycol di(meth)acrylate (the number of carbon atoms being 2 to 20), ethyleneglycol oligomerdi(meth)acrylate (2 to 10 quanta), bisphenol A di(meth)acrylate, 2,2-bis[p-(γ-methacryloxy-62-hydroxy-propoxy)phenyl]propane, 2,2-di(4-methacryloxypolyethoxyphenyl)propane (2 to 10 etoxy groups in one molecular), trimethyloolpropantri(meth)acrylate, and pentaerythrytol tetra(meth)acrylate; urethane (meth)acrylic acid esters which are a reaction product between 2 moles of (meth)acrylate having hydroxyl groups and 1 mole of diisocyanate, specifically, monomers such as disclosed in the Japanese Patent Publication No. 55-33687 or the Japanese Laid-open Patent Publication No. 56-152408. These monomers may be employed singly or in the form of a mixture of two or more of those monomers. The monomer is preferably employed in a quantity of 10 to 50 wt % in the composition.

The polymerization initiator or a catalyst which may be employed in the photo-polymerizable composite resin may be any known polymerization initiator such as, for example, α-diketone and tertiary amine such as disclosed in the Japanese Laid-open Patent Publications No. 48-49875 and No. 60-26002, or α-diketone and peroxide such as disclosed in the Japanese Laid-open Patent Publications No. 57-203077 and No. 60-149603. The catalyst is employed in a quantity within the range of 0.1 to 5 wt % based on the weight of the polymerizable monomers.

The filler material which may be employed in the photo-polymerizable composite resin includes various inorganic, organic or inorganic and organic composite filler materials. Specific example thereof includes a silicone dioxide (quartz, quartz glass or silica gel) or alumina. Further, for the inorganic filler material, various glasses containing silicone as a principal component with various heavy metals, boron and/or aluminum, various ceramics, clay minerals such as diatom earth, karione or monmolinite, active white earth, synthetic zeolite, mica, fluorinated calcium, calcium phosphate, barium sulfate, zirconium dioxide, titanium dioxide may also be employed.

For a surface treatment of the filler, any known silane coupling agent may be employed which may include organic silicone compounds such as, for example, ω-methacryloxyalkyltrimethoxysilane (the number of carbon atoms between the methacryloxy group and the silicone atom being 3 to 12), vinyltrimethoxysilane, vinyltriethoxysilane, vinyltriacetoxysilane.

The photo-polymerizable composite resin which is employed in the practice of the present invention may, if desired, contain various known additives including, for example, a stabilizing agent and/or one or more pigments.

BRIEF DESCRIPTION OF THE DRAWINGS

The present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention. In the accompanying drawings, like reference numerals are used to denote like parts throughout the several views, and;

FIG. 4A is a schematic side view of a modified form of the light-curing apparatus shown in FIG. 1A, which is employed in an example used to demonstrate the present invention; and FIG. 4B shows that distal end of an optical fiber in greater detail;

DETAILED DESCRIPTION OF THE EMBODIMENTS

Figure 1A:
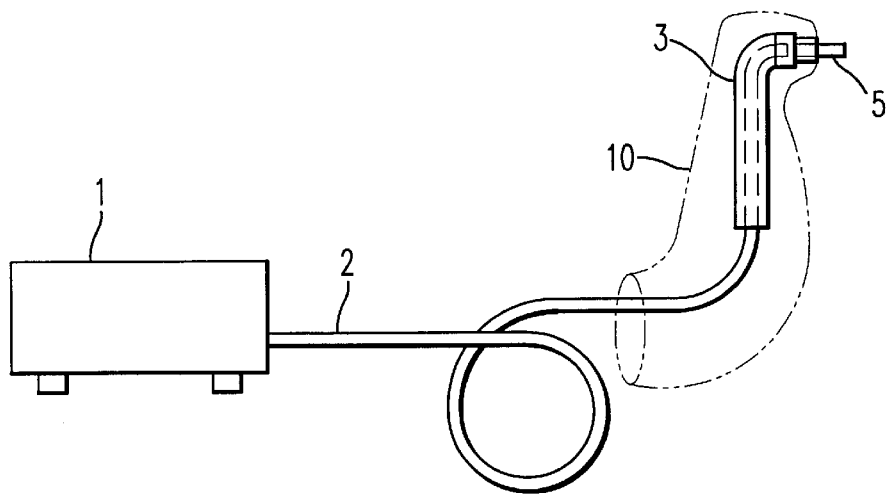
FIG. 1A is a schematic diagram showing a light-curing apparatus for dental use according to a first preferred embodiment of the present invention.
Figure 1B:
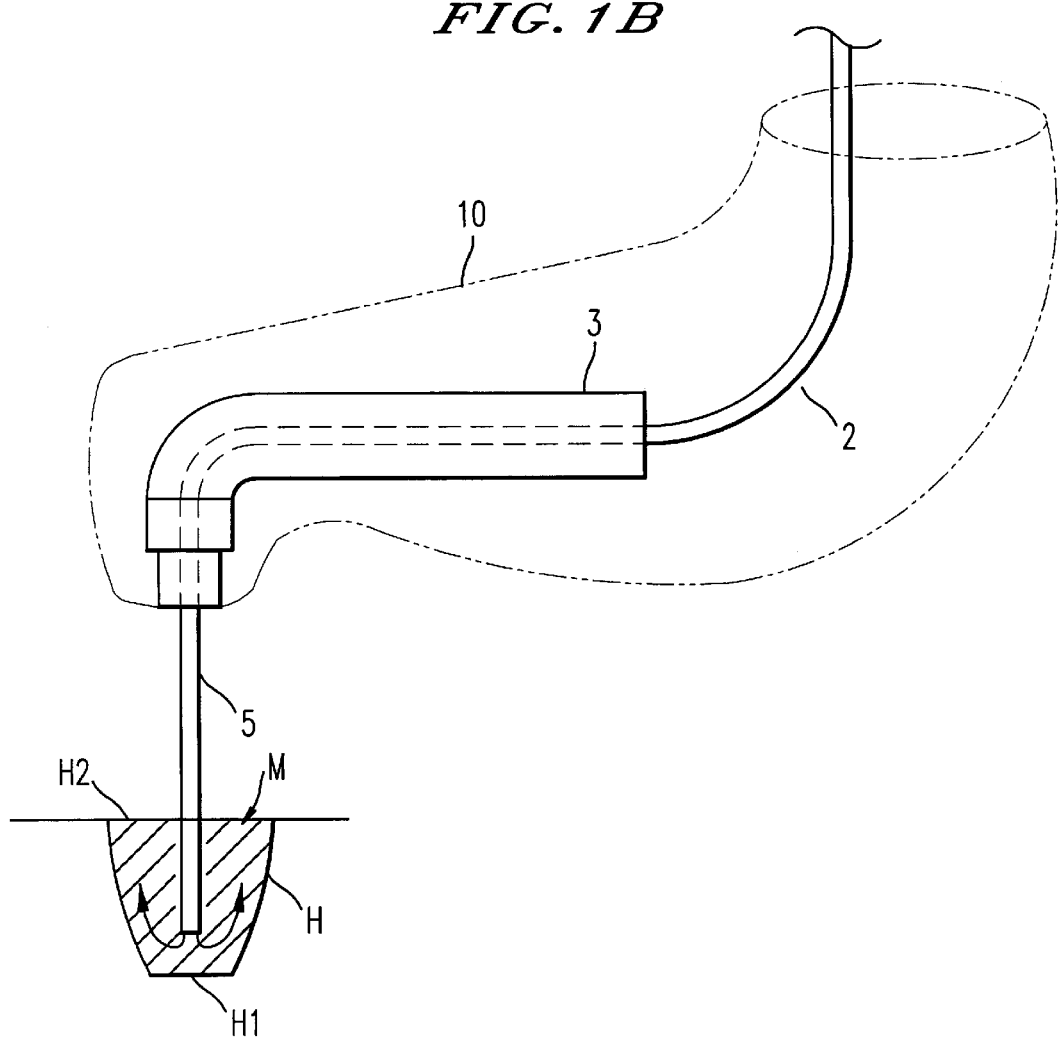
FIG. 1B is a schematic side view, on an enlarged scale, of a distal portion of the light-curing apparatus shown in FIG. 1A, showing a distal end of an optical fiber forming the light-curing apparatus inserted in a cavity filled with a photo-polymerizable composite resin.

FIG. 1A illustrates a light-curing apparatus according to a first preferred embodiment of the present invention. The light-curing apparatus shown therein comprises a laser light source 1, and an elongated light guide means 2 such as an optical fiber having an end optically coupled with the light source 1 and a distal end or a light emitting element 5 adapted to be inserted into the bottom of the photo-polymerizable composite resin M filled in a cavity H as shown in FIG. 1B during the dental treatment. The light-curing apparatus also comprises a handpiece 3 adapted to be gripped by a dentist and mounted on a portion of the light guide means 2 adjacent the distal end 5 thereof. The handpiece 3 in the illustrated embodiments also serves as a covering for that portion of the light guide means 2. A hand covering or an auxiliary covering 10 made of polyethylene is provided to enclose the handpiece 3 except for the distal end 5 of the light guide means 2 for protecting both of the handpiece 3 and the hand of the dentist from being contaminated in the mouth of a patient being treated.

When in use, the dentist has to insert his hand into the hand covering 10 and then grips the handpiece 3. As shown in FIG. 1B, the distal end 5 of the light guide means 2 is, after the handpiece 3 has been aimed at a caries-affected tooth within the mouth of a patient, inserted deep into the cavity H to a position adjacent the bottom of the cavity H so that the photo-polymerizable composite resin M filling up the cavity H can be polymerized progressively from a portion H1 of the filled composite resin adjacent the bottom of the cavity H towards a surface portion H2 of the filled composite resin M adjacent the surface of the tooth when light from the light source is introduced through the light guide means 2.

Figure 2:
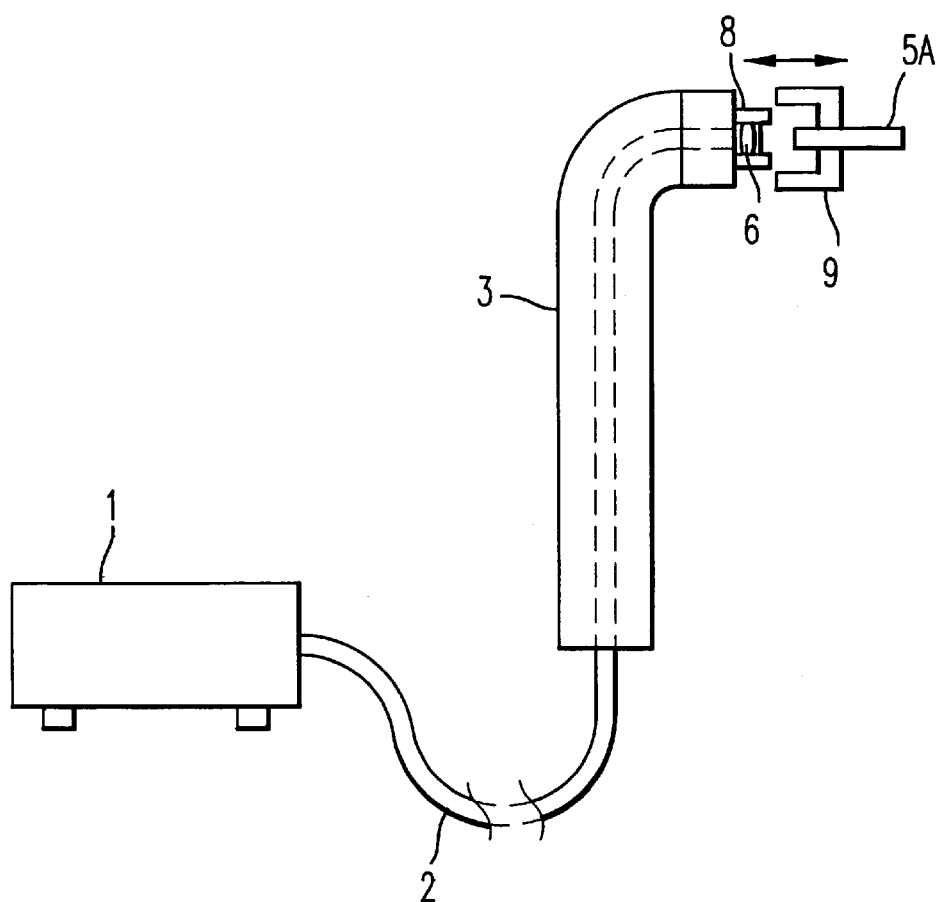
FIG. 2 is a schematic diagram showing the light-curing apparatus according to a second preferred embodiment of the present invention.

FIG. 2 illustrates the light-curing apparatus according to a second preferred embodiment of the present invention. In this embodiment, contrary to the first embodiment, the light emitting element 5A is a separate part from the light guide means 2, and the light guide means 2 employed in this embodiment of FIG. 2 has its distal end terminating generally in flush with a distal end face of the handpiece 3. A light collecting means 6, which may be a conductor lens element, is fitted to the distal end face of the handpiece 3 by means of a mount frame 8 carrying the light collecting means 6.

The light-curing apparatus according to the second preferred embodiment also comprises a generally cap-like adaptor or a rotating connector 9 adapted to be detachably capped externally onto the mount frame 8 by means of, for example, screwing or bayonet coupling. The adaptor 9 forms a detachable optical coupling mechanism and includes a light emitting element 5A such as an optical fiber which is coupled optically with the distal end of the light guide means 2 through the light collecting means 6. In this case, the light guide means 2 may be a rod or a tube made of transparent plastics.

Figure 3:
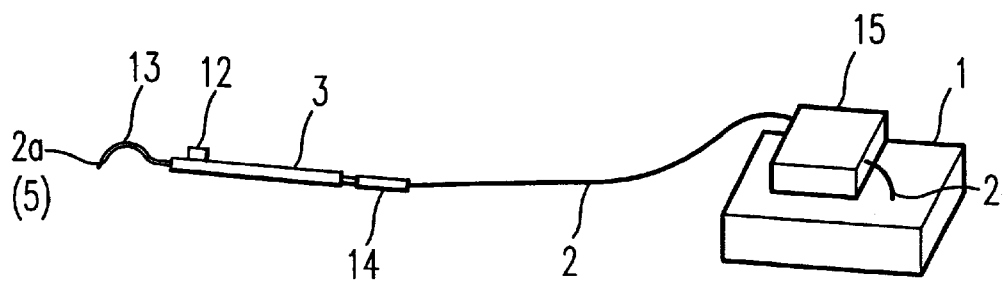
FIG. 3 is a schematic diagram showing the light-curing apparatus according to a third preferred embodiment of the present invention.

The light-curing apparatus according to a third preferred embodiment of the present invention is shown in FIG. 3. This light-curing apparatus comprises a laser light source 1, an elongated light guide means 2 in the form of a single continuous optical fiber, a handpiece 3 mounted on a portion of the light guide means 2 adjacent a distal end 2a of the light guide means 2, an optical fiber cutting button 12 mounted on a distal end portion of the handpiece 3 and serving as a fiber cutter, a guide sheath 13 in the form of a metallic tube for guiding the distal end 2a of the light guide means 2, an additional covering 14 made of plastics for preventing the light guide means 2 from being contaminated in contact with the mouth of a patient, and an optical fiber reel 15 mounted atop the laser light source 1 for reeling the light guide means 2.

The light guide means 2 (the optical fiber in this case) drawn outwardly from the optical fiber reel 15 is passed through and retained in position within a hollow of the guide sheath 13 after having been passed through the covering 14 and the handpiece 3 with the distal end 2a forming the light emitting element 5 exposed outwardly from the guide sheath 13. When the dentist pushes the fiber cutting button 12, a cutter blade (not shown) is advanced within the handpiece 3 to cut the light guide means 2 to separate the distal end 2a from the light guide means 2. When a pushing force applied to the fiber cutting button 12 is released, the cutter blade is automatically retracted to an inoperative position by the action of a biasing spring (not shown).

The distal end 2a of the light guide means 2 so cut from the remaining portion of the light guide means 2 after the dental treatment is contaminated and may therefore be discarded. After the distal end 2a has been discarded, the dentist may pull the light guide means 2 from the reel 15 to allow a fresh distal end 2a to be exposed outwardly from the guide sheath 13.

The present invention will now be demonstrated by way of some illustrative examples which are not intended to limit the scope of the present invention.

EXAMPLE

In this example, the light-curing apparatus was utilized of a structure which comprises, as shown in FIG. 4A, a solid state user 1 made of a semi-conductor capable of oscillating light of 473 nm in wavelength as a secondary harmonic wave and wherein the laser beam so generated from the solid state laser 1 is guided to a short optical fiber 5B forming the light emitting element through the light guide means 2. In this light-curing apparatus shown in FIG. 4A, the light guide means 2 and the short optical fiber 5B are employed in the form of optical fibers made of quartz and acrylic plastics, respectively. The short optical fiber 5B is removably inserted into a distal end of the handpiece 3 for optical coupling with a distal end of the light guide means 2 aligning the axis of both optical fibers, as shown in greater detail in FIG. 4B.

A commercially available photo-polymerizable dental composite resin. "CLEARFILL AP-X (A2 Colors)", was filled in a transparent glass tube, as a replacement of a dental cavity, of 10 mm in diameter and 10 mm in depth and an optical fiber of 0.5 mm in diameter (ESCA, manufactured by and available from Mitsubishi Rayon Co., Ltd., Japan) was subsequently inserted into the center of the transparent glass tube. The dental composite resin within the glass tube was irradiated by light of 36 mW for a various length of time as shown in Table 1 below. Subsequently, the dental composite resin cured and sticking to the ESCA fiber is removed out of the glass tube and an unpolymerized portion of the composite resin adhered to the outer surface of the cured composite resin was removed by an alcohol-soaked tissue paper. The cured composite resin has exhibited a generally spherical form, the diameter of which was measured by a micrometer. Measurement results are shown in Table 1.

TABLE 1

| Irradiating Time (sec) | 2 | 3 | 5 | 7 | 10 | 20 |
|---|---|---|---|---|---|---|
| Diameter of Cured Resin (mm) | 4.0 | 4.4 | 5.4 | 6.0 | 6.4 | 7.8 |

As a result of the experiments, it has been exhibited that the photo-polymerizable dental composite resin was cured progressively from a portion thereof adjacent the incident light and that the light emitted to the photo-polymerizable composite resin was so sufficiently scattered as to lose the orientation and the directionality of the light.

EXAMPLE 2

Figure 5A:
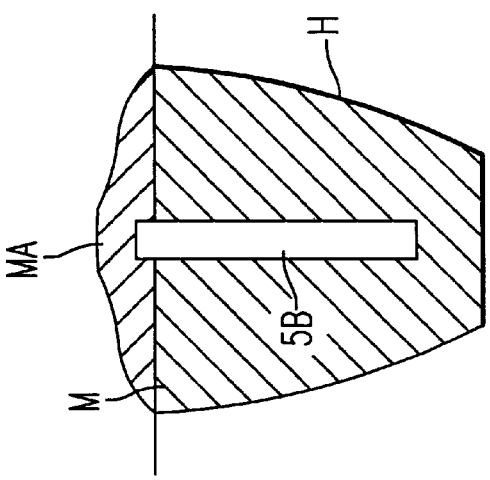
FIGS. 5A to 5C are schematic sectional representations showing the sequence of an exemplary dental treatment performed with the use of the light-curing apparatus of the present invention.
Figure 5B:
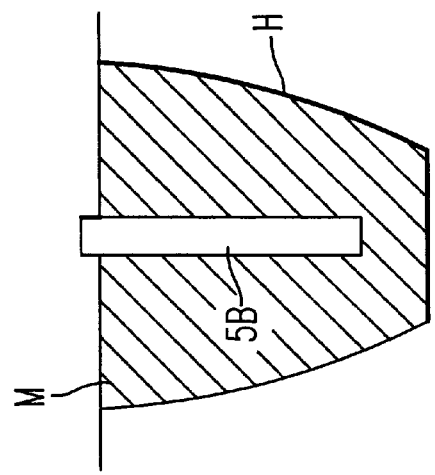
Figure 5C:
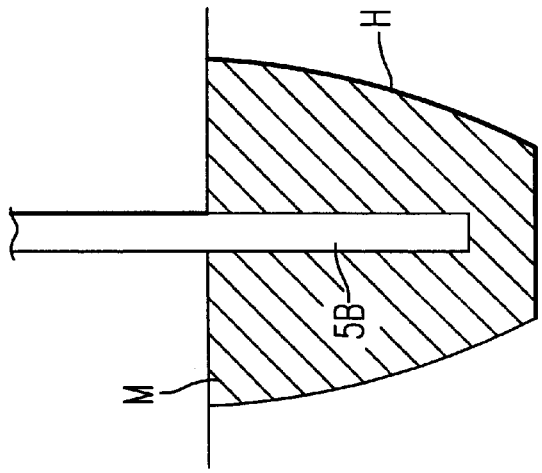

A first-class cavity of 5 mm in diameter and 4 mm in depth was formed in an occlusal part of an extracted fresh human molar and a slightly small quantity of the photo-polymerizable composite resin, the same as that used in Example 1, was filled in the cavity together with the same binding agent as in Example 1. After the filling, the ESCA fiber 5B forming a part of the light emitting element described in Example 1 was inserted deep into the cavity H so as to reach a position adjacent the bottom thereof as shown in FIG. 5A and the filled composite resin M was irradiated for 20 seconds. Thereafter, as shown in FIG. 5B, the ESCA fiber 5B was cut at a position substantially level with the top surface of the filled composite resin M, and as shown in FIG. 5C, an additional amount of the same photo-polymerizable composite resin M was added to the top surface of the filled composite resin M to form a resin overlay MA to render the extracted human molar to represent a crown shape.

The resin overlay MA was subsequently irradiated from above with the laser beam emitted from the light-curing apparatus to thereby complete the dental restoration. Thereafter, the restored human molar was subjected to a thermal cycle test for 1,000 cycles. One cycle of the test consist of holding the sample at 4° C. for one minute and then holding it at 60° C. for one minute. As a result of the thermal cycle test no separation of the cured composite resin from the human molar was found.

After the thermal cycle test, the restored human molar was immersed in an aqueous solution of 0.1% basic fuchsine at 37° C. for one day, and was then cut into halves. Observation of a cut face of each half of the restored human molar has shown no dye penetration and no gap found.

COMPARISON

A cavity of the same size as that in Example 2 was formed in an extracted human molar and was subsequently filled with the same photo-polymerizable composite resin as that in Example 2 by the use of the same bonding agent as that in Example 2. Using a commercially available light-curing apparatus. "SPECTRUM" (available from Dentsply. Light Intensity 700 mW/cm$^2$), the light was projected for 20 seconds from a position 3 mm above the filled composite resin to initiate polymerization of the filled composite resin. As a result of the irradiation, white concentric circle lines were found on the surface along the margin of the cavity. When the human molar having the composite resin filled therein was immersed in an aqueous solution of 0.1% basic fuchsine for one day, penetration of red dyes along the white circle lines was observed.

EXPERIMENT 3

As shown in FIG. 3, using the same laser light source 1 as that in Example 1, the laser beam was guided directly to the polyurethane-cladded acrylic optical fiber 2 (ESCA, available from Mitsubishi Fayon Co., Ltd., Japan). The light-curing apparatus was of the structure similar to that shown in FIG. 3 and in which the distal end 2a of the optical fiber 2 protrudes 6 mm outwardly from the distal end of the handpiece 3. The long optical fiber 2 was wound compact around the optical fiber reel 15 mounted atop the light source 1 of the light-curing apparatus and only a necessary length thereof was drawn out of the optical fiber reel 15 during the use thereof.

A first-class cavity of 4 mm in diameter and 3 mm in depth was formed on an occlusal part of a patient's molar and both of the bonding agent and the composite resin same as those used in Example 2 were filed in the cavity. The distal end 2a of the optical fiber 2 of the light-curing apparatus was subsequently inserted to a position adjacent the bottom of the cavity and the laser beam was irradiated for 20 seconds to cure the composite resin. After curing of the composite resin, the distal end 2a of the optical fiber 2 was removed out of the patient's molar leaving a hollow column in the cured composite resin. An additional amount of the same composite resin was subsequently applied in the hollow column and also over the top surface of the cured composite resin to form a resin overlay to render the patient's molar to represent a crown shape similar to the original shape.

Thereafter, using the same light-curing apparatus, the optical fiber was positioned 3 mm above the cavity in the patient's molar and the laser beam was irradiated for 20 seconds to cure the composite resin which had been additionally filled.

After the dental restoration treatment, the distal end 2a of the optical fiber 2, which appeared to have been contaminated by the patient's body fluid was cut for disposal, and the handpiece 3, the guide sheath 13 and the additional covering 14 were sterilized in readiness for the subsequent use.

Although the present invention has been fully described in connection with the preferred embodiments thereof with reference to the accompanying drawings which are used only for the purpose of illustration, those skilled in the art will readily conceive numerous changes and modifications within the frame-work of obviousness upon the reading of the specification herein presented of the present invention. Accordingly, such changes and modifications are, unless they depart from the scope of the present invention as delivered from the claims annexed hereto, to be construed as included therein.

What is claimed is:

1. A dental light-curing apparatus, which comprises:
   a light source for generating a laser beam having a wavelength ranging from 350 to 500 nm at 10 to 100 mW; and
   an elongated light guide means having a proximal end optically coupled with the light source and having a light emitting element at a distal end thereof, at least said light emitting element being an optical fiber which emits the laser beam from the end portion thereof and adapted for introduction into a photo-polymerizable dental composition which fills a cavity in a dental mold or a tooth, thereby enabling irradiation of the photo-polymerizable dental composition at a location adjacent the bottom of the dental cavity, wherein said light emitting element has a length sufficient to penetrate through the cavity from its opening to reach said adjacent location and has a diameter not greater than 1.5 mm.

2. The dental light-curing apparatus as claimed in claim 1, further comprising a detachable optical coupling mechanism interposed between the light emitting element and the distal end of the light guide means to permit the light emitting element to be selectively coupled to and decoupled from the light guide means.

3. The dental light-curing apparatus as claimed in claim 1, further comprising a cutting mechanism for cutting the light guide means to separate the light emitting element from the light guide means.

4. The dental light-curing apparatus as claimed in claim 1, wherein at least said light emitting element has a surface having an affinity to the photo-polymerizable dental composition.

5. The dental-curing apparatus as claimed in claim 1, wherein at least said light emitting element has a surface having no affinity to the photo-polymerizable dental composition.

6. The dental light-curing apparatus as claimed in claim 1, further comprising a contamination-preventive covering to prevent the light guide means from being contaminated.

7. A dental light-curing apparatus, which consists essentially of:
   a light source which generates a laser beam having a wavelength ranging from 350–500 nm at 10 to 100 mW; and
   an elongated light guide means having a proximal end optically coupled with the light source and having a light emitting element at a distal end thereof, at least said light emitting element being an optical fiber which emits the laser beam from the end portion thereof and adapted for introduction into a photo-polymerizable dental composition which fills a cavity in a dental mold or a tooth, thereby enabling irradiation of the photo-polymerizable dental composition at a location adjacent the bottom of the dental cavity, wherein said light emitting element has a length sufficient to penetrate through the cavity from its opening to reach said adjacent location and has a diameter not greater than 1.5 mm.

* * * * *